US009889316B2

(12) United States Patent
Imran

(10) Patent No.: US 9,889,316 B2
(45) Date of Patent: *Feb. 13, 2018

(54) METHODS FOR DELIVERY OF OPTICAL SIGNALS TO TISSUE FOR THE TREATMENT OF A DISEASE OR CONDITION

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/094,048

(22) Filed: Apr. 8, 2016

(65) Prior Publication Data

US 2016/0279441 A1    Sep. 29, 2016

Related U.S. Application Data

(60) Continuation of application No. 14/944,577, filed on Nov. 18, 2015, now Pat. No. 9,333,373, which is a (Continued)

(51) Int. Cl.
*A61N 1/00* (2006.01)
*A61N 5/06* (2006.01)
(Continued)

(52) U.S. Cl.
CPC ......... *A61N 5/0622* (2013.01); *A61N 1/0529* (2013.01); *A61N 1/36* (2013.01);
(Continued)

(58) Field of Classification Search
USPC .................................... 607/36–37
See application file for complete search history.

(56) References Cited

U.S. PATENT DOCUMENTS 5,693,435 A    12/1997   Amatucci et al.
5,750,926 A    5/1998    Shulman et al.
(Continued)

OTHER PUBLICATIONS

International Search Report and Written Opinion and Notice dated Jun. 1, 2010 for International Application PCT/US2009/062392.
(Continued)

*Primary Examiner* — Nicole F Johnson
(74) *Attorney, Agent, or Firm* — Mahamedi IP Law LLP; Joel Harris

(57) ABSTRACT

Embodiments described herein provide methods for treating various conditions and diseases using an optical signal. In one or more embodiments an apparatus is providing having an optical window, which is used to deliver an optical signal to provide stimulation to one or more tissue sites in the body such as the brain, optic nerve, eye, ganglia, spine, or other like site. The optical signals can be used to treat a variety of neurological diseases and conditions including epilepsy, migraine headaches and chronic pain. In particular applications the optical signals can be used to treat, inhibit or prevent epileptic or other neurological seizures by providing an optical input to a foci or surrounding tissue in the brain causing the seizure. The optical signal may also be combined with an electrical signal to produce an aggregate effect in tissue for treating the disease or condition such as a neurological disease or condition.

24 Claims, 27 Drawing Sheets

Related U.S. Application Data division of application No. 13/710,407, filed on Dec. 10, 2012, now Pat. No. 9,220,916, which is a continuation of application No. 12/265,690, filed on Nov. 5, 2008, now Pat. No. 8,332,037.

(51) Int. Cl.

| | | |
|---|---|---|
| *A61N 1/375* | (2006.01) | |
| *A61N 1/36* | (2006.01) | |
| *H01R 13/52* | (2006.01) | |
| *A61N 1/05* | (2006.01) | |
| *A61N 1/37* | (2006.01) | |

(52) U.S. Cl.
CPC ......... *A61N 1/36064* (2013.01); *A61N 1/375* (2013.01); *A61N 1/3754* (2013.01); *A61N 5/0601* (2013.01); *H01R 13/5224* (2013.01); *A61N 1/0536* (2013.01); *A61N 1/37* (2013.01); *A61N 2005/063* (2013.01); *H01R 2201/12* (2013.01)

(56) References Cited

U.S. PATENT DOCUMENTS

| | | | |
|---|---|---|---|
| 5,861,019 A | | 1/1999 | Sun et al. |
| 5,902,326 A | * | 5/1999 | Lessar .................... A61B 5/031 600/333 |
| 5,987,358 A | | 11/1999 | Sosebee et al. |
| 6,198,445 B1 | | 3/2001 | Alt et al. |
| 6,459,935 B1 | * | 10/2002 | Piersma ............... A61N 1/3754 257/E23.114 |
| 6,658,287 B1 | * | 12/2003 | Litt ...................... A61B 5/0476 600/544 |
| 6,975,906 B2 | | 12/2005 | Rusin et al. |
| 7,396,265 B2 | | 7/2008 | Darley et al. |
| 2005/0024837 A1 | | 2/2005 | Youker et al. |
| 2006/0009813 A1 | | 1/2006 | Taylor et al. |
| 2006/0259093 A1 | | 11/2006 | Stevenson et al. |
| 2007/0060970 A1 | | 3/2007 | Burdon et al. |
| 2007/0123949 A1 | | 5/2007 | Dabney et al. |
| 2007/0179554 A1 | * | 8/2007 | Iyer ..................... A61N 1/3754 607/37 |
| 2007/0277374 A1 | | 12/2007 | Suaning |
| 2008/0049376 A1 | | 2/2008 | Stevenson et al. |
| 2008/0065181 A1 | | 3/2008 | Stevenson |
| 2008/0140148 A1 | | 6/2008 | Rogier |
| 2008/0140149 A1 | * | 6/2008 | John .................... A61N 1/0529 607/45 |
| 2009/0156912 A1 | * | 6/2009 | Kuhn ................... A61B 5/0086 600/310 |
| 2009/0187229 A1 | | 7/2009 | Lavie |
| 2009/0258519 A1 | | 10/2009 | Dilmaghanian et al. |

OTHER PUBLICATIONS

European Search Report dated Jan. 28, 2014 in Application No. 09825246.3.

* cited by examiner

Schematic Diagram of Telemetry Circuit

METHODS FOR DELIVERY OF OPTICAL SIGNALS TO TISSUE FOR THE TREATMENT OF A DISEASE OR CONDITION

RELATED APPLICATIONS

This application is a continuation of U.S. patent application Ser. No. 14/944,577, filed Nov. 18, 2015, now U.S. Pat. No. 9,333,373 issued May 10, 2016, which is a divisional of U.S. patent application Ser. No. 13/710,407, filed Dec. 10, 2012, now U.S. Pat. No. 9,220,916 issued Dec. 29, 2015, which is a continuation of U.S. patent application Ser. No. 12/265,690 filed Nov. 5, 2008, now U.S. Pat. No. 8,332,037 issued Dec. 11, 2012, entitled "HOUSING STRUCTURE FOR A MEDICAL IMPLANT INCLUDING A MONOLITHIC SUBSTRATE"; the aforementioned applications being hereby incorporated by reference herein in their entirety for all purposes.

FIELD OF THE INVENTION

Embodiments described herein relate to housing structures for medical implants. More specifically, embodiments described herein relate to housing and lid structures for hermetically sealed medical implants such as pacemaker housings.

BACKGROUND

Medical implants are being used with increasing frequency to treat a variety of conditions from heart disease, to chronic pain and Parkinson's disease. A number of these implants include electronic circuitry for providing a pacing signal or other electrical stimulation of body tissue and/or monitoring a physiological function such as heart rate. Typically, the electronic circuitry for these devices is contained in a hermetically sealed housing to protect the circuitry from exposure to fluids and humidity present within the environment of the body. This circuitry is coupled to one or more pacing or other leads which are coupled to a connector (known as a header for pacemaker applications) that sits typically on the top portion of the housing. The header includes wiring that must be passed through the top the housing while still maintaining the hermetic seal. This may require one or more glass to metal or other labor intensive seals which are difficult and costly to manufacture. Wires that pass through the housing often must be reconnected to a flex circuit or other internal connector coupling the wires to the internal circuitry. This internal connector takes up space in the housing making the housing larger. This can be less than desirable since in many applications, the housing is desirably fabricated as small as possible to so as to be implanted in an unobtrusive manner in pockets of fatty tissue in the patient's chest or abdomen. Additional constraints on available space within the housing can result from the fact that since the housing is often made of a conductive metal, no circuitry can be placed on the housing. Thus, there is a need for a housing cover or lid for pacemaker and other medical implants which allows for low cost electrical seals for pass through wiring and electrical connections and increases the amount of available space within the housing.

BRIEF DESCRIPTION OF THE DRAWINGS

FIG. 10a is a top view illustrating a top substrate layer, including an antenna. FIG. 10b is a top view illustrates an interior layer having a first capacitor plate. FIG. 10c is a top view illustrating another interior layer having a second capacitor plate. FIG. 10d is a top view illustrating a bottom layer including an inductor, a connector architecture for an attached device and an attached device. FIG. 10e is a cross sectional view of the multilayer substrate illustrating stacked substrate layers as well as attached components and devices.

DETAILED DESCRIPTION OF THE INVENTION

Figure 1:
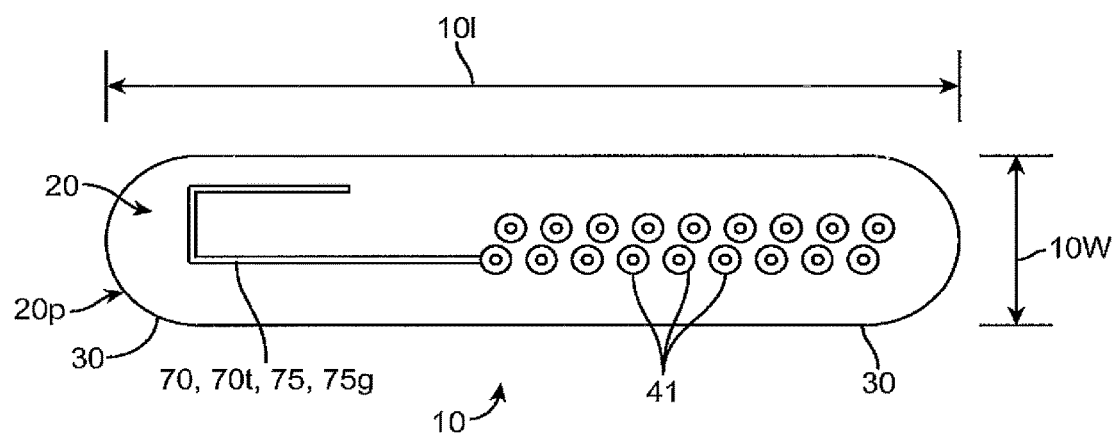
FIG. 1 is a plan view of a lid structure including an antenna according to an embodiment of the invention.

Embodiments described herein provide lid and housing structures for various medical electronic implants housings including cardiac implants such as pacemakers, gastric implants, spinal implants and neural implants. Many embodiments include a lid or other cover structure that allows one or more electrical components to be fabricated on a surface or interior of the lid structure so as to improve the utilization of space within the housing available for electronic circuitry and reduce the number of separately assembled electronic components. Various embodiments also provide a lid structure including a plurality of vias with connecting pins projecting through and hermetically sealed to the vias to reduce manufacturing cost and time of making hermetically sealed pass through electrical connections to electronic circuitry in the housing.

In one embodiment, the invention provides a lid structure for a medical implant housing comprising a monolithic substrate comprising a dielectric material, a conductive portion fabricated on at least one of the top or bottom surfaces or an interior of the substrate, a frame at least partially surrounding a perimeter of the substrate, an antenna positioned on a top surface of the substrate, a plurality of vias projecting at least partially through the substrate, a plurality of conductive pins with at least one of the conductive pins projecting through a via. The pins which typically comprise a conductive metal such as platinum or a platinum iridium alloy, are desirably configured to engage electrical connectors contained in a separate connecting structure which sits atop the housing. The frame which typically comprises titanium or other biologically inert metal, is hermetically joined to the substrate using brazing, such as gold brazing, or other joining method. It is also configured to be hermetically joined to the implant housing by brazing or other joining method.

In various pacemaker applications, the lid structure can be configured to be hermetically sealed to the pacemaker housing or container (known as a can). In these and related embodiments, this can be facilitated by the frame including a lip or flange which engages the pacemaker and can subsequently be hermetically sealed to the can by brazing or other joining method. Additionally, in various pacemaker applications, the lid structure including the pins, can be configured to be coupled to the pacemaker header or other related connector structure which sits atop the pacemaker. The pins are desirably configured to engage or otherwise be coupled to one or more female connectors in the header which are connected to the pacemaker leads. Alternatively, the pins can be directly coupled to the lead connectors.

In another embodiment, instead of forming part of a lid structure that is in turn joined to the housing, the substrate can be directly and hermetically joined to the housing so that the substrate is integral to the housing and forms part of the housing wall. In these and related embodiments, the substrate can be hermetically joined to a frame which is then hermetically joined a housing body which includes an opening that is shaped to receive the frame. Alternatively, the substrate can be directly joined to the shaped opening.

The substrate typically comprises one or more dielectric materials known in the art such as various dielectric ceramics. In some embodiments, the substrate can be fabricated from a substantially optically transparent material such as glass or one or more optically transparent dielectric polymers. Use of optically transparent materials for the substrate allows for the creation of an optical window in the substrate which can be used as an optical conduit or coupling for optical sensing of physiologic data (e.g., oxygen saturation), sending and receiving signals for optical communication and for delivering an optical stimulation or pacing signal to a desired tissue site. Embodiments employing optical communication can be used to communicate various data from the pacemaker (or other device) to an external communication device as well as for reprogramming the pacemaker.

In various embodiments of a method of using a pacemaker (or other stimulating device) housing having an optical window, the window can be used to sense physiologic data which is then used as input to modulate the pacing signal generated by the pacemaker. This input can be supplemental to input received from the pacemaker leads or depending upon the sensed data (e.g., a sudden decrease in blood pressure or $PO_2$ levels), can actually become the primary input or otherwise over ride data input from the leads. Various control algorithms can be employed to assign a weighting to the optical data input relative to the lead input and determine what conditions will initiate an override. In another embodiment, the optical window can be used to deliver an optical stimulating signal to a tissue site such as the brain. This signal can be delivered along with an electrical signal also generated by stimulating device or another device. The two signals can be synchronized to produce an aggregate effect.

In one embodiment, a physiological function is paced by (i) providing or positioning a pace maker apparatus to pace the physiological function, the pace maker including a housing having an optical window, the apparatus configured to generate a pacing signal; and (ii) optically sensing physiologic data through the optical window; and modulating the pacing signal in response to the sensed physiologic data.

In still another embodiment, a biological tissue is stimulated by (i) providing or positioning a stimulator apparatus to operate in or on the biological tissue, the stimulator apparatus including a housing having an optical window, the apparatus configured to generate a stimulation signal; and (ii) delivering an optical stimulation signal to tissue through the optical window.

The conductive portion will typically comprise a conductive metal such as copper, gold, platinum or like metal which can be applied using photolithography methods known in the art. It allows electrical components to be fabricated on and/or coupled to the top or bottom surface or interior of the substrate. Multiple conductive portions can be fabricated on the substrate to fabricate one or more electronic components such as capacitors, resistors and inductors and circuits using these components. For example, two conductive portions can be placed at a selectable distance across the thickness of the substrate to construct a capacitor, while a third conductive portion can be used to construct an inductor. Multiple components can be so fabricated to construct one or more of an LC, RC, or LRC circuit. Such circuits can be coupled to the connecting pins to provide a filtering function (e.g., high pass, low pass, etc) or other function for each pin or a selectable group of pins. In this way, the space requirements within the housing can be reduced because such circuits which would typically require multiple separate components can now be fabricated directly on the substrate with no separate connector. Also the components and circuits fabricated on the substrate can form an integral part of circuitry within the implant housing. For example, one or more components fabricated on the substrate (e.g., capacitors, inductors, etc.) can be an integral part of a pacing, sensing, power or other circuit. Again, such integral configurations can achieve space and cost savings because the need for multiple separate electrical components and associated connections is reduced.

In particular embodiments, the conductive portion can be used to fabricate an antenna on a top surface of the substrate. The antenna comprises a conductive trace fabricated on a top surface of the substrate. The antenna is configured to send and receive signals between the medical implant when it is implanted in the body of a patient and a communication device external to the patient's body such as a PDA, portable computer or other communication device. Use of such an integral antenna reduces the number of separate components for the implant and the associated manufacturing cost. The antenna can be sized and otherwise configured to send and receive signals in a selectable frequency range such as the 400 MHz to 6 GHz frequency range with a specific embodiment of 402 to 405 MHz corresponding to the MICS standard established by the FCC. Other frequency ranges are also contemplated corresponding to one or more standards for medical electronics or related products. This can be achieved by fabricating the antenna to have one or more turns and selection of the permittivity of the substrate which in specific embodiments, can be greater than 5, 10 or 30 with high permittivity values achievable through use of a ceramic substrate such as alumina zirconia or combinations thereof. In various embodiments, the conductive portion can also be configured to be used as an electrical connector to couple one or more separate components and devices to the lid structure. Such components can include capacitors, inductors resistors, diodes etc, while the devices can include microprocessors, ASIC, DSPs and memory devices. In these and related embodiments, the conductive portion can be configured to have a pattern or architecture for making specific connections to specific components (e.g., capacitors) and devices (e.g., microprocessors). One example of such a connector architecture can comprise a pattern of traces configured to align with the pins or connectors of a microprocessor or ASIC. Other patterns can be employed for other devices. The pattern of traces can be produced using photolithography or like methods.

Figure 2:
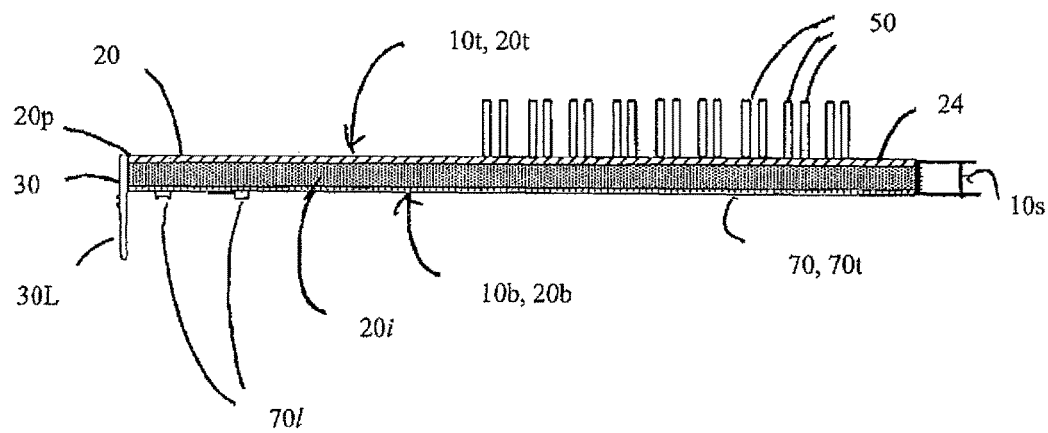
FIG. 2 is a side view of the embodiment of FIG. 1.

Embodiments described herein provide a lid structure for a medical implant (MI) housing or container for MI devices such as cardiac pacemakers, defibrillators, gastric pacemakers, neural stimulators and other like devices. Referring now to FIGS. 1-3, preferred embodiments of a lid structure 10 (also described herein as cap or cover structure 10) for use with a MI housing will typically include a monolithic substrate 20 (also known as substrate 20), a frame 30, a plurality 41 of vias 40 and pins or other connecting elements 50 (also referred to as connectors 50) at least one of which extends through the vias. Substrate 20 which will typically comprise one or more dielectric materials known in the art, includes a conductive portion 70. Frame 30 can comprise titanium, steel or other metal and will typically be gold brazed to substrate 20, though other metallurgical joining techniques are also contemplated. Typically, frame 30 extends all the way around the perimeter 20P of substrate 20, but it may, in some embodiments, extend only partway around perimeter 20P. Also as is described herein, frame 30 may extend below the bottom side of the antenna so as to have a lip or flange 30L. Frame 30 including lip 30L can be constructed by molding, machining, stamping or other metallurgical fabrication known in the art.

Substrate 20 includes an interior 20i, a top surface 20t positioned on a top side of 10t of lid 10 and a bottom surface 10b positioned on a bottom side 10b of the lid (for purposes of special reference, top and bottom surfaces 20t and 20b are also sometimes referred to herein as top and bottom sides 20t and 20b). Accordingly, in various embodiments, conductive portion 70 can be positioned on the top or bottom substrate surface 20t or 20b or interior 20i. Also, multiple conductive portions 70 can be fabricated at each of these locations to construct one or more electrical components as is described herein.

Substrate 20 can comprise one or more dielectric materials including various dielectric ceramics known in the art. Also, the substrate desirably has a permittivity and size allowing embodiments of antenna 70a discussed herein to be sized to fit onto the substrate top surface to send and receive signals in a selected frequency range such as the 402 to 405 MHz frequency range. In various embodiments, the permittivity of the substrate 20 can be greater than 1, 5, 10 or 30. In specific embodiments, the permittivity can be in the range from 1-10, 10-20, 20-30 and 30-50. This can be achieved through the selection of one or more high permittivity ceramics such as alumina or zirconia or other material known in the art. The permittivity of the substrate material can also be selected for sizing the antenna for communication in other frequency ranges such as 30 to 300 MHz, 300 MHz to 3 GHz, and 3 GHz to 30 GH. Also in various embodiments described herein, substrate 20 can comprise one or more optically transparent dielectric materials such as glass or glass like materials, so as to allow for an optical window for the passage of various wavelengths of light through the substrate.

Vias 40 will typically be through vias going from top side 20t of the substrate to the bottom side 20b. However, blind vias and buried vias are also contemplated. The vias 40 can be produced by laser or other drilling method known in the art. Typically, vias 40 will include gold or other conductive metal plating and can include pads 41 on both sides of the substrate. The number of vias 40 can be in the range of 4 to 30 with specific embodiments 10, 12, 14, 16, 18 and 20. Other numbers of vias are also contemplated. Vias 40 are desirably dimensioned to allow pins 50 to project through or into the via. Vias 40 can be coupled to pins 50 by brazing, soldering or other joining method known in the art so as to hermetically seal the via with the pin in place. In other embodiments, vias 40 can comprise a blind via going from substrate surface 20t or 20b into substrate interior 20i to allow access to a conductive layer 70 positioned in the substrate interior. They can also be hidden vias to allow access between two or more conductive portions 70 positioned within the substrate interior 20i.

Typically, the conductive portion 70 will comprise one or more conductive metals such as copper, gold, silver, platinum and alloys thereof. The use of conductive polymers and semi-conductive materials is also contemplated. The conductive portion can also comprise a single or multiple layers of conductive or semi-conductive material. Also multiple conductive portions 70 can be fabricated at multiple locations on or within substrate 20 to fabricate various electrical components and provide conductive locations for attachment of electrical components and devices.

In many embodiments, conductive portion 70 can comprise one or more conductive traces 70 which can have a variety of shapes and patterns. Trace 70t can be varied in thickness from the micron to the mm level and can have a variety of shapes including linear, rectangular, U-shaped, circular or like shape. The trace can be printed on substrate 20 or applied through various photolithographic techniques known in the art.

Portion 70 including traces 70t can be shaped and otherwise configured to fabricate one or more electrical components 75 discussed herein, as well as serving as connecting locations or features 70I for various externally attached electrical components and devices. In particular embodiments, connecting location 70l can be configured to have an architecture or pattern for aligning to the connecting pins of a microprocessor or other electronic device or component. In various embodiments, conductive portion 70 including traces 70t can be fabricated at a selected location on or in substrate 20 using various printing, laser jet printing, or photo-lithography methods known in the art (e.g., via the use of masks and photoresist).

An exemplary embodiment of a method of fabrication of lid or other structure 10 including a monolithic substrate 20 will now be presented. This method including the order of operations is exemplary with other methods and sequences equally applicable. First, vias 40 could be drilled in the substrate using laser drilling or other drilling method. Then the conductive portions 70 comprising one or more components 75 could be printed or otherwise fabricated on the top, bottom or other surface of the substrate. Pins 50 could then be brazed or otherwise attached to vias 40 and the entire substrate 20 could be brazed or otherwise attached to frame 30. Finally, components 75 or circuits 76 could be attached to conductive portions on the bottom side 20b of the substrate.

Figure 3A:
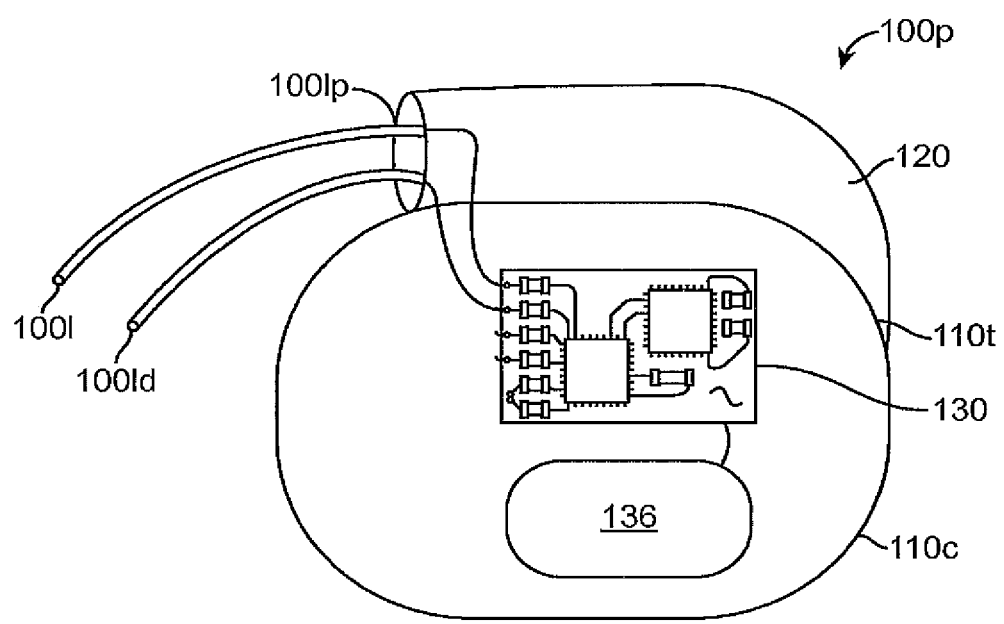
FIG. 3a is a perspective/schematic view showing the construction of a typical pacemaker.
Figure 3B:
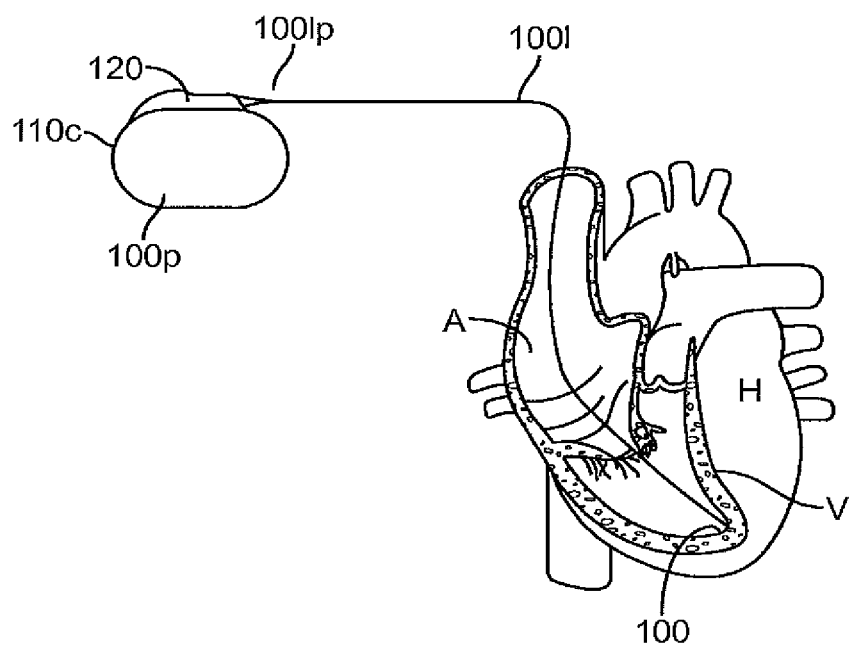
FIG. 3b illustrates the connection of a pacemaker to the heart.

Various embodiments of lid structure 10 can be configured to be attached to a number of medical implant housings and containers described herein and known in the art including cardiac, gastric, brain and spinal implants. For purposes of illustration, a discussion will now be presented of the attachment of structure 10 to a cardiac pacemaker housing 110c. However, it should be appreciated that pacemaker housing 110c is exemplary and other medical implant housings having different shapes and comprising different materials are equally applicable. Referring now to FIGS. 3a-3b, the typical pacemaker 100p includes a housing 110 which typically comprises a metal container known as a can 110c. Can 110c contains various electronic components and circuitry 130 such as sensing, pacing and power circuitry, as well as a battery or other stored power supply 136. Many pacemakers will also include a header 120 which sits atop can 110c and includes one or more connectors 120c for coupling to pacemaker leads 100l that are positioned within a chamber of the heart H such as the Atria A or ventricle V.

Figure 4:
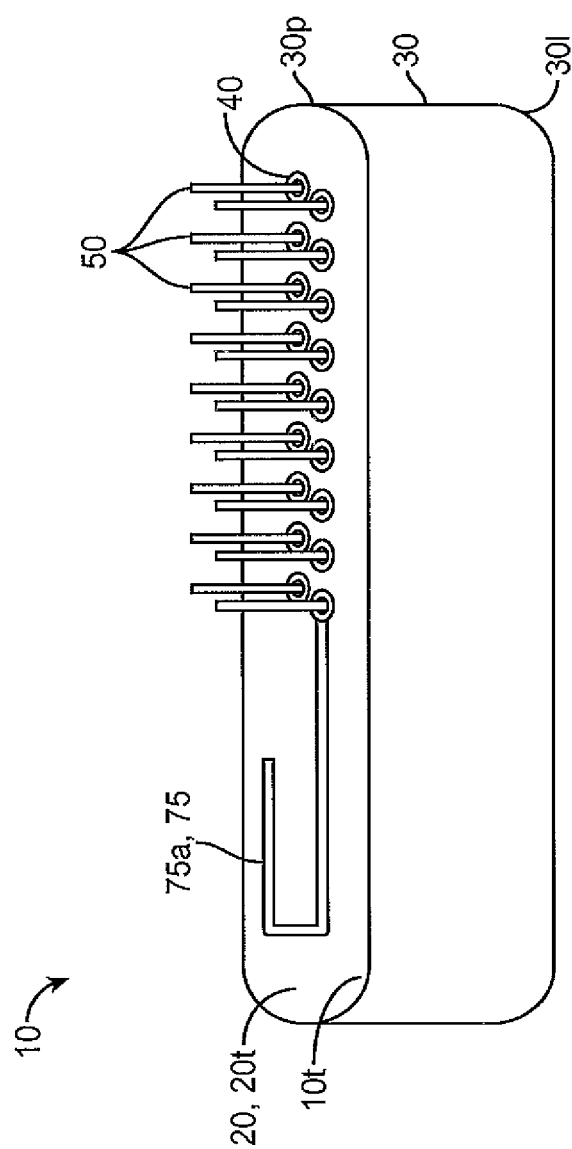
FIG. 4 is a perspective view of an embodiment of the lid structure which can coupled to a pace maker housing.
Figure 5A:
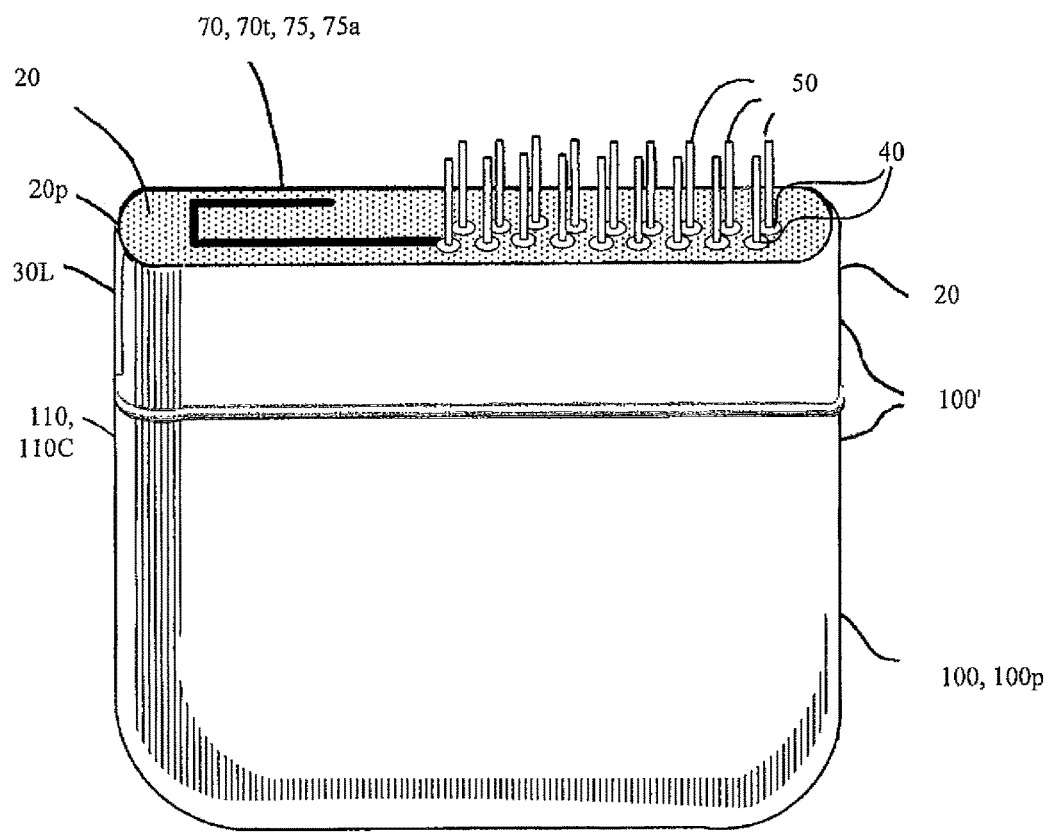
FIG. 5a is a perspective view illustrating the placement of the lid structure on a pace maker housing.
Figure 5B:
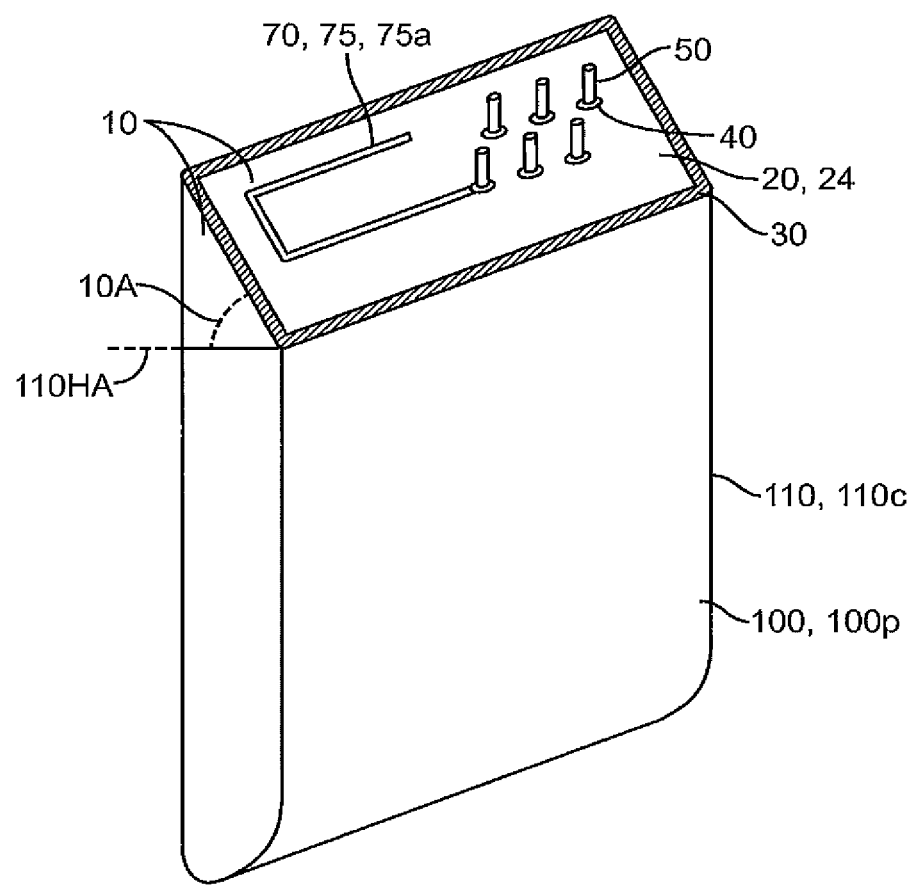
FIG. 5b is a perspective view illustrating the placement of the lid structure at angle on the pace maker housing.
Figure 6:
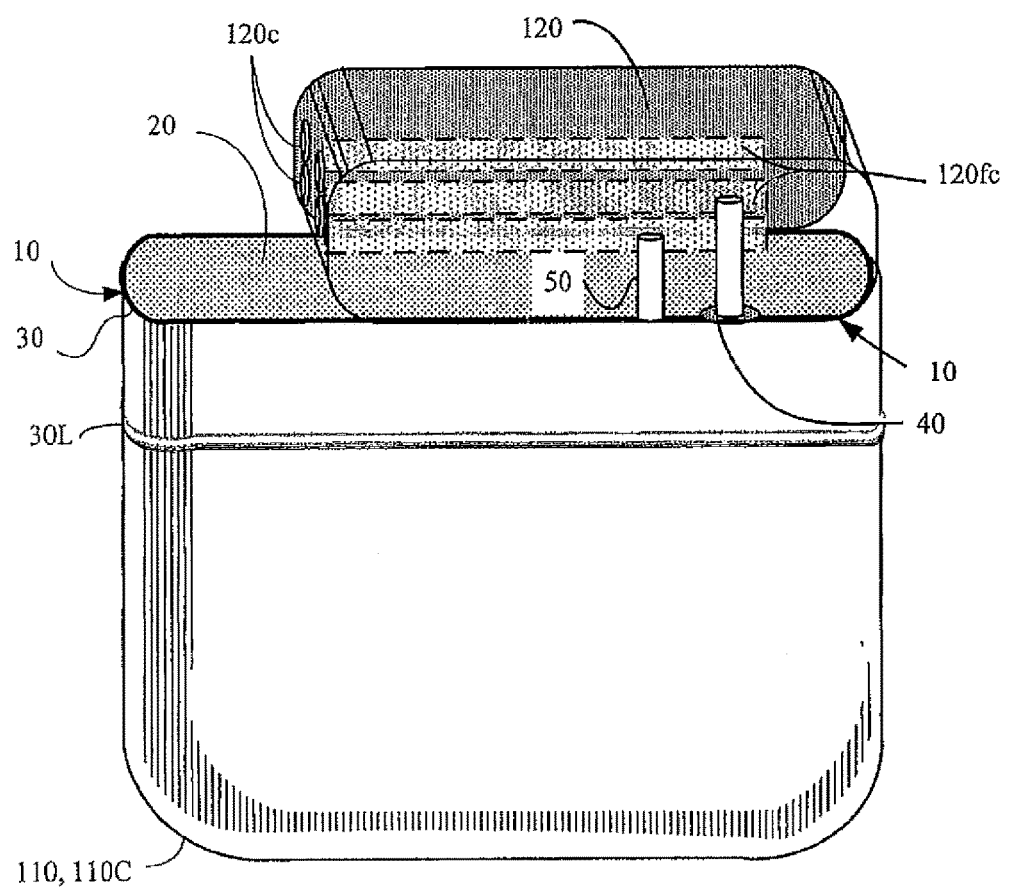
FIG. 6 is a perspective view illustrating the engagement of the lid structure with a header connector.

Referring now to FIGS. 4-6, in particular embodiments, lid structure 10 is configured to be joined to a pacemaker can 110c or other implant housing 110 so as to form a completely enclosed container; however, non-enclosed embodiments are also contemplated. Also, the lid structure 10 is desirably hermetically sealed to can 110c so as to prevent the ingress of both liquid water and water vapor which may damage electrical components and circuitry of the pacemaker. This is achieved by hermetically sealing frame 30 to can 110c. Since frame 30 and can 110c are typically made of a biologically inert metal such as titanium, hermetic sealing of these two components can be achieved by brazing or through the use of other metallurgical joining methods known in the art. In various embodiments, this can be facilitated by constructing the frame to have a lip or inner flange 30 L which fits into or over can 110c or other housing 110 as is shown in FIG. 4. FIG. 5a shows such a lid structure 10 attached to the can. Other joining methods (e.g., adhesive bonding or RF and ultrasonic welding) are also contemplated where one or both of the frame or housing are constructed from a polymer or other non-metallic material.

Lid structure 10 can have variety of shapes, but will typically have a thin oblong oval shape, other shapes are also contemplated. Typically, lid structure 10 will have a flat profile but it may also be curved. The size and shape of structure 10 are configured to be able to mate to a selected housing 100, while controlling the shape of the assembled housing 100' or otherwise not significantly increasing its form factor so that it can fit in a desired implant site. In various embodiments, the length 10L of the structure 10 can be in the range of 10 to 100 mm with specific embodiments of 40 and 60 mm. The width 10W can be in the range of 5 to 40 mm with specific embodiments of 10 and 30 mm. The thickness 10S can be in the range of 0.25 to 2 mm with specific embodiments of 0.5, 0.75, 1.25 and 1.5 mm.

In various embodiments, lid structure 10 can be configured to be attached in any number of orientations with respect to can 110c or other housing 110. In the embodiment shown in FIG. 5a, lid structure 10 can be positioned substantially parallel with respect to the horizontal axis 110ha of housing 110. In other embodiments shown in FIG. 5b, the lid structure can be positioned attached at a selectable angle 10a with respect of axis 110ha. Angle 10a can be in the range from 1 to 80°, with specific embodiments of 30, 45 and 60°. Use of an angled lid structure including substrate 20 allows for substrate having larger surface area (with respect to top opening 110t of the housing) which allows for increased area for fabrication and attachment of components to the substrate. It also provides for additional space within the housing for the components of the pacemaker 100 or other medical implant.

For many pacemakers, in addition to a can 110c, the pacemaker also includes a connector assembly known as a header 120 that typically sits atop can 110c and includes one or more connectors 120c for connecting to a pacemaker lead 100l. Accordingly, in addition to being configured to be coupled to the pacemaker can 110c, in various pacemaker applications, lid structure 10 including pins 50 be configured to be coupled to the pacemaker header 120, as is shown in FIG. 6, or other related connector structure which sits atop the pacemaker. Pins 50 are desirably configured to engage or otherwise be coupled to one or more female connectors 120fc in the header which are connected to the pacemaker leads 110l. Alternatively, the pins can be directly coupled to the lead connectors.

Figure 7A:
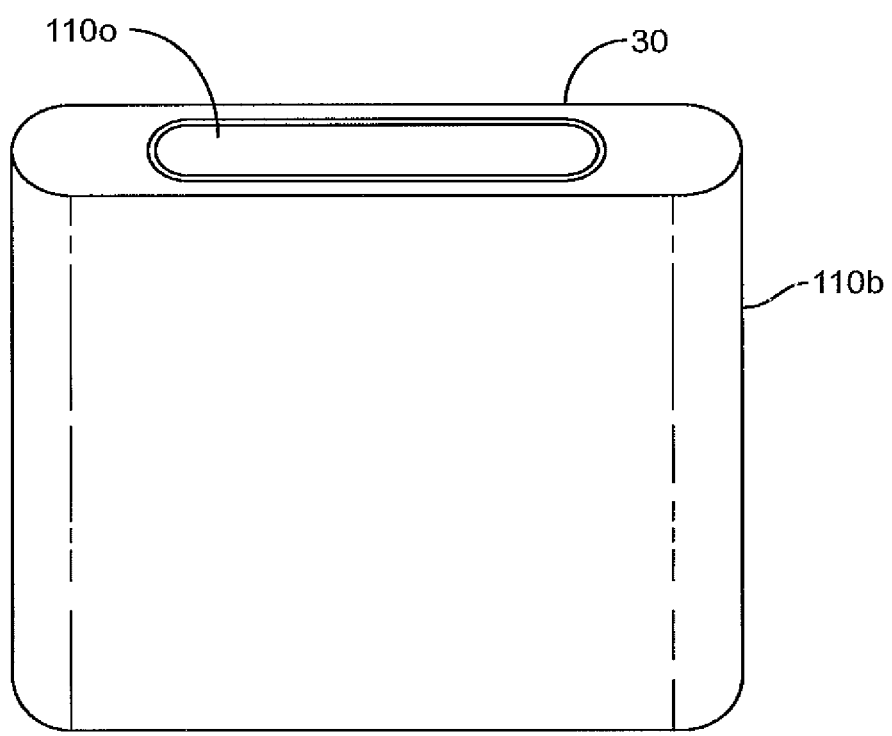
FIG. 7a is a perspective view illustrating an embodiment of a housing body for a pacemaker or other medical implant housing including an opening sized for placement of a monolithic substrate (with or without a frame).
Figure 7B:
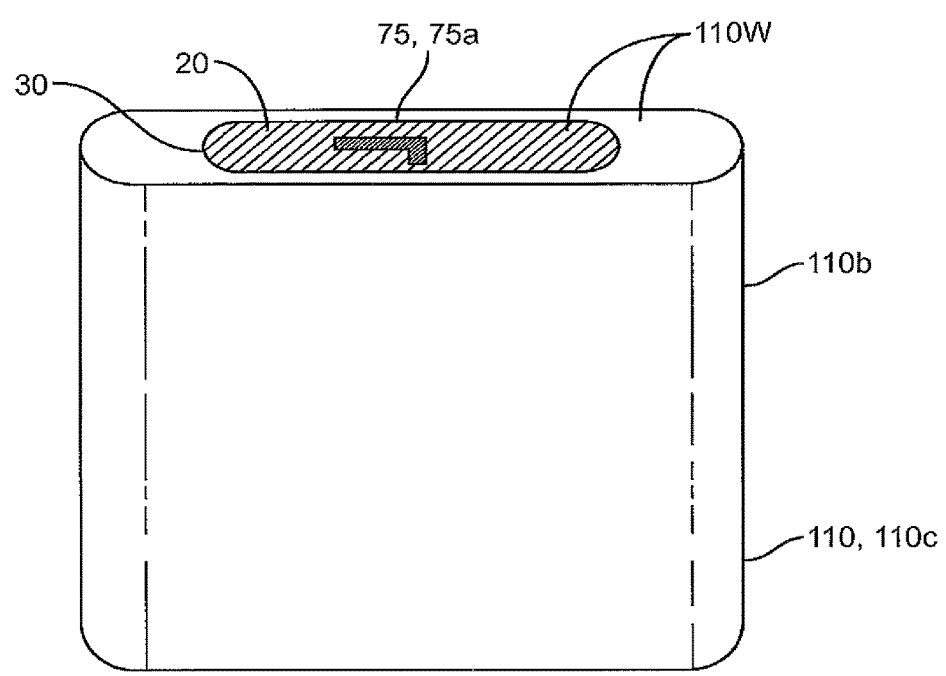
FIG. 7b is a perspective view illustrating an embodiment of a monolithic substrate joined to the housing body of FIG. 7a so as to form an integral structure.
Figure 7C:
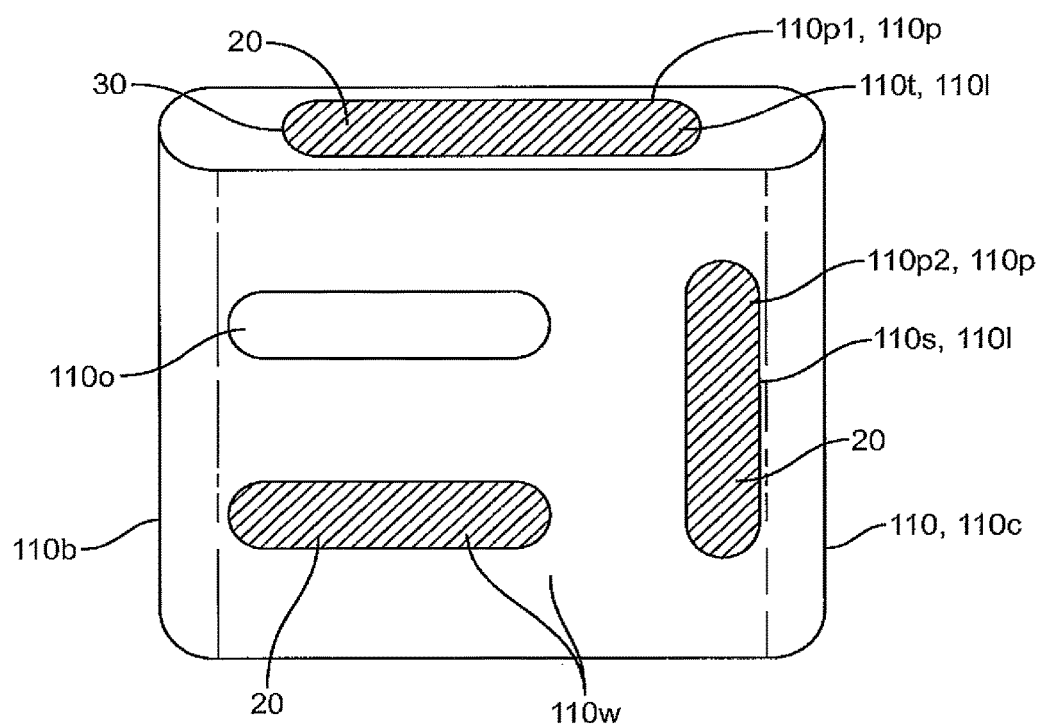
FIG. 7c is a perspective view illustrating an embodiment of a medical implant housing including multiple monolithic substrate sections joined to the housing.
Figure 7D:
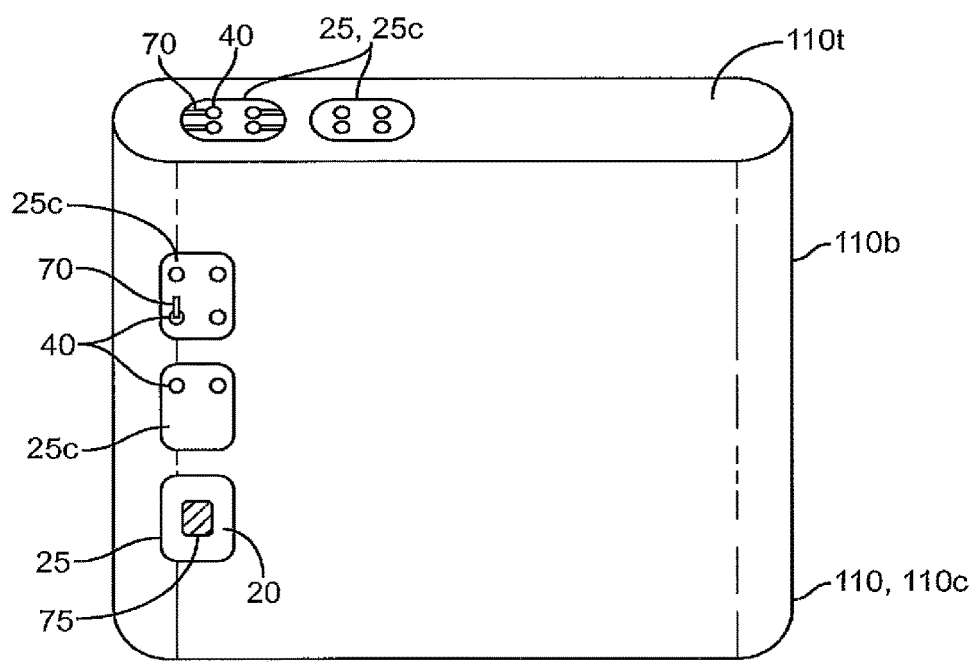
FIG. 7d is a perspective view illustrating an embodiment of a medical implant housing including multiple monolithic substrate sections with conductive pins.

Referring now to FIGS. 7a-7d, instead of forming part of a lid structure that, is in turn, joined to housing 110, in some embodiments, the substrate can be directly and hermetically joined to the housing 110 so that the substrate 20 is integral to the housing and forms part of the housing wall 110w as shown in FIG. 7b. In these and related embodiments, the substrate can be hermetically joined to a frame 30 which is then hermetically joined to a housing body 110b which comprises the housing 110 with an opening 110o that is shaped to receive the frame or as is shown in FIG. 7a (alternatively, substrate 20 can be directly joined to housing body 110b). Also in various embodiments, substrate 20 can be positioned at any number of locations on housing 110 including sides 110s with housing body 110b including a space 110o for the positioning of the substrate. Again, in such embodiments, the substrate can include one or more attached components 75 or circuits 76 allowing for modular assembly of any number of circuits and components of implant 100. Also, multiple monolithic substrates 20 can be positioned in multiple locations 100l on housing 110 including locations in a different spatial planes 110p including at least a first and second plane 110p1 and 110p2. Such locations 110l can include the top 110t and sides 110s of the housing as is shown in FIG. 7c.

Embodiments having multiple substrates 20 allow for the positioning of pins or other connecting elements 50 in multiple locations on the housing. In use, such embodiments can facilitate connection of the housing to one or more leads 100l both in terms of manufacturability and reliability. For example, instead of having to direct all of the leads to one central connector location on the housing such as top 110t, the proximal end 100lp of the lead (which is the end of the lead attached to can 10c or other housing 110) can now be positioned at a location on the housing which is closest to the distal end 110ld of the lead or otherwise involves lesser amounts of bending of the lead. This reduces the length of the lead and also reduces various forces on the lead including one or more of the amount of tension, compression or torsion the lead is subject to. This in turn, improves lead reliability by reducing the likelihood of the lead distal end from being dislodged from the target site, (e.g., the atria), or disconnected from the pacemaker at the proximal lead end. It also reduces incidence of shearing or other lead mechanical failure due to the reduced force applied on the lead.

In various embodiments of a medical housing 110 having multiple substrates 20, the substrates may of a specific type or section 25 including a selected set of components such as connector elements 50, electrical components 75 or architecture 78 (discussed herein) for a particular location. For example, one embodiment of substrate type 25 shown in FIG. 7d may include a connector substrate 25c that includes selected number of connector elements 50 (along with conductive traces to one or more elements 50) so as to make a connection to housing 110 at a selection location 110l. Multiple connector substrate sections 25c can be positioned in proximity or in different locations on the housing to produce a selected configuration of connector elements 50 (e.g., two side by side sets of 4 pins). In use, such embodiments facilitate customized fabrication of housing 110 by allowing placement of connective elements 50 at selected locations on the housing using off the shelf substrate sections.

Figure 7E:
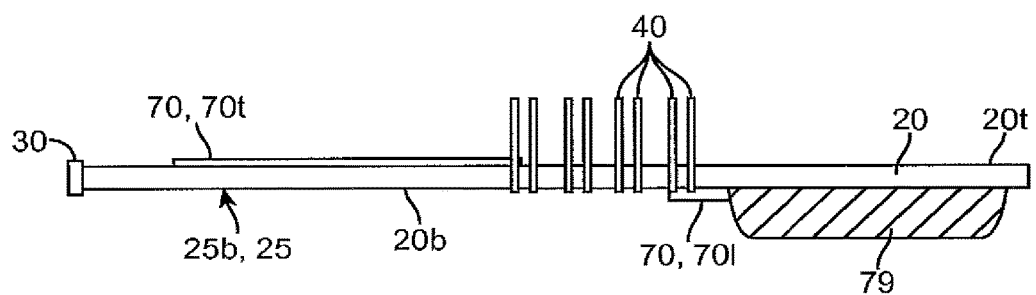
FIG. 7e is a side view illustrating another embodiment of a substrate for attachment to a medical implant housing, with this embodiment including an attached battery.

Another embodiment of a particular substrate type 25, can include a battery substrate 25b, in which substrate 20 includes a battery or other power supply 79 positioned on a bottom surface 20b of the substrate as is shown in FIG. 7e. Similar to the preceding embodiment, this embodiment allows the positioning of a battery 79 or multiple batteries 79 at any number of locations on the housing. Further, such embodiments allow for the positioning of battery(ies) 79 at locations within the housing which allow for improved packing efficiency within the housing, e.g., the shape of the battery correlates to the shape of the space, and/or the battery can be positioned in open space locations in the housing which were previously inaccessible without the use of the substrate section 25b.

Figure 7F:
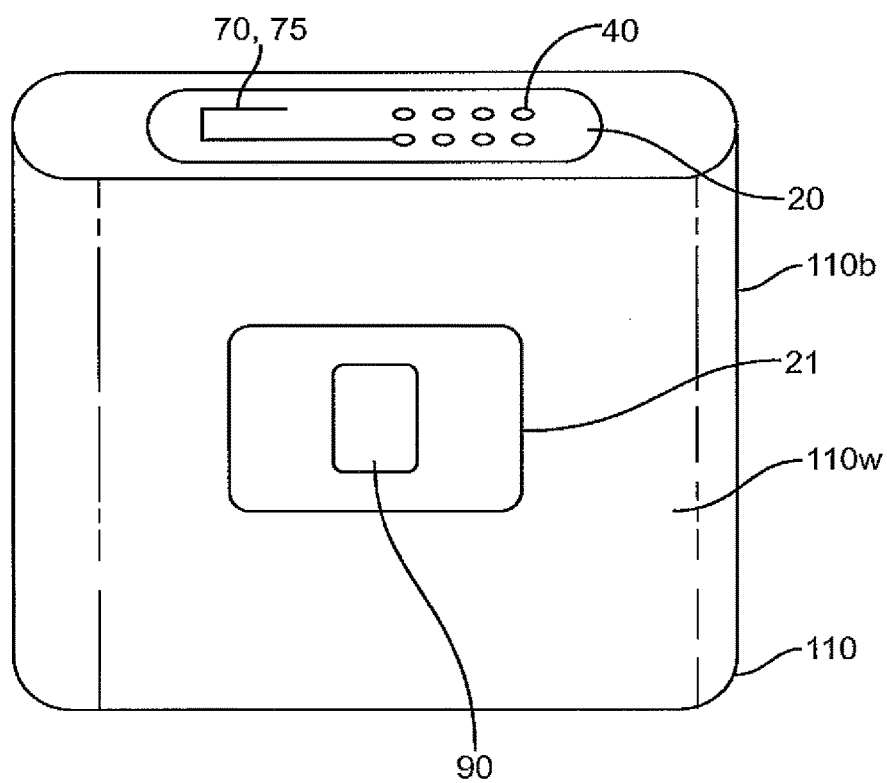
FIG. 7f is a perspective view illustrating an embodiment of an optically transparent substrate section joined to a housing body.
Figure 7G:
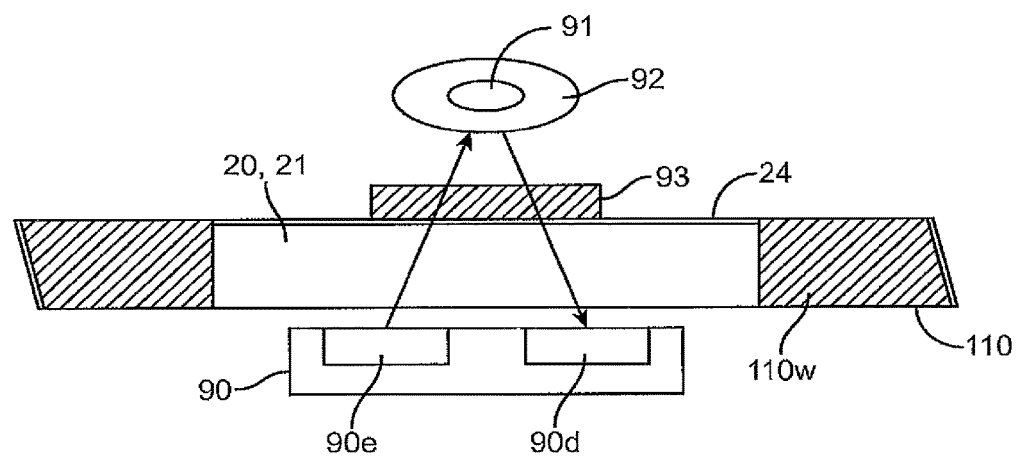
FIG. 7g is a side view illustrating placement and use of an emitter and detector with an optically transparent substrate for in vivo sensing from the within a medical implant housing.

In particular embodiments, all or a portion of substrate 20 can be fabricated from optically transparent materials such as glass, quartz or a transparent biocompatible polymer known in the art so as to comprise an optical window 21 that allows for transmission of light through window 21 as is shown FIG. 7f. Window 21 can be configured for a variety of uses including sensing and optical communication. In sensing applications, the window can configured to allow for optical sensing of various physiological parameters, such as blood glucose, blood oxygen saturation, etc. This can be achieved through the use of an optical device 90 including emitter 90e such as a diode and a detector 90d such as a photomultiplier as is shown in FIG. 7g. Emitter and detector 90e and 90d can be configured for the emission and detection of a wavelength for detection of a desired physiological analyte 91 (e.g., blood glucose) or detection of a particular cell type 92 or an amount of thrombus, collagen or other bio-layer attached to the housing.

Figure 7H:
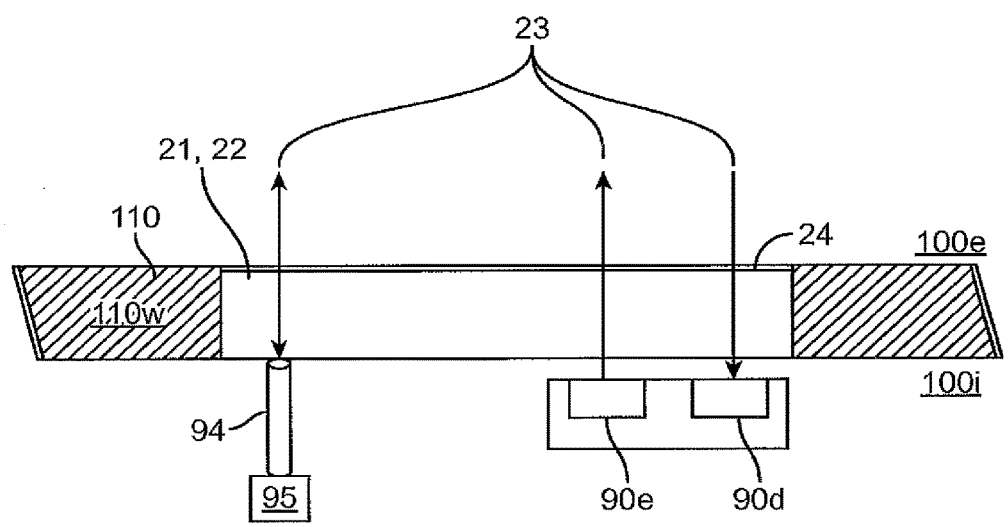
FIG. 7h is a side view illustrating use of an optically transparent substrate as an optical coupling for optical communication between the interior and exterior of a medical implant housing.

In another embodiment shown in FIG. 7h, window 21 can configured as an optical coupling 22 for sending and receiving and receiving optical signals 23 between the housing interior 100i and the housing exterior 100e. This can be achieved through the use of a fiber optic or other optical conduit 94 positioned beneath the window which leads to an optical switch or communication device 95 or an optical detector 90d and emitter 90e positioned beneath the window.

In particular embodiments where the implant is positioned transdermally, optical communication with implant 100 can be achieved through the use of infrared or other wavelengths of light that are transmitted through the skin. In such applications, an external fiber optic or other optical communication device is positioned adjacent or in close proximity to the layer of skin overlying the optical 21 window of the implant housing.

Embodiments of optical window 21 can be employed as an optical coupling 22 to allow for one or more of the following functions: i) communication of data from the pacemaker to an external monitoring device; ii) communication of programming from an external computer to allow for reprogramming of the pacemaker software stored in logic or memory resources; iii) optical sensing of various physiological data by sensing the site around the implant; and iv) transmission of an optical stimulating or pacing signal to surrounding or other tissue. External optical communication can be achieved through use of fiber optic devices such as a fiber optical catheter or like device that is positioned within proximity of the implant site.

Figure 7I:
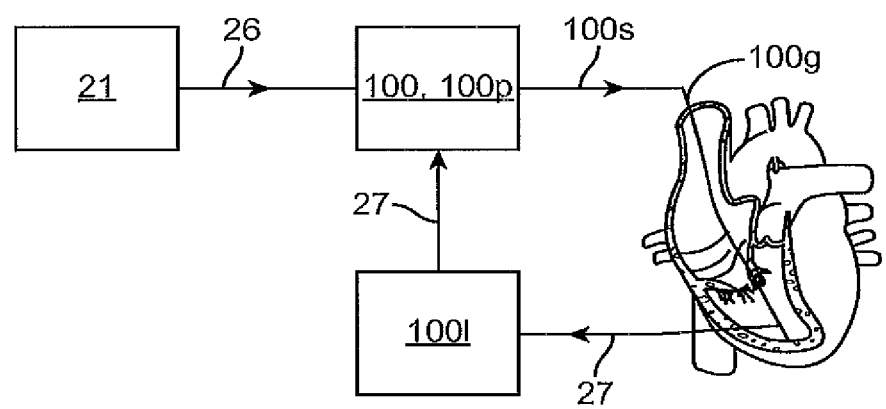
FIG. 7i is a block diagram illustrating use of physiological data sensed through an optically transparent substrate as an input to modulate a pacing signal.
Figure 7J:
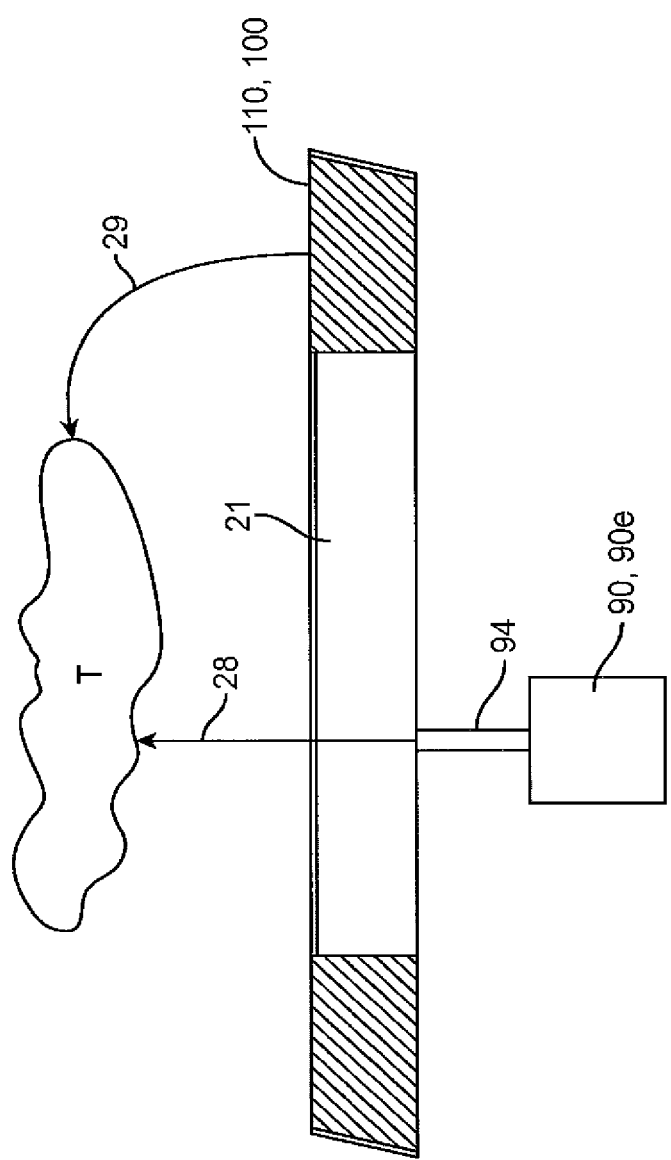
FIG. 7j is a side view illustrating use of optical signals sent through and optically transparent substrate to stimulate and/or treat a tissue site.

Referring now to FIG. 7i, in various sensing applications using window 21, physiological data that are sensed through optical window 21 can be used as an input 26 to modulate or otherwise control pacing signals 100s sent out by pacemaker or other device 100. Input 26 can be used to supplement electrical inputs 27 received from pacing leads 100l to control pacing signals 100s or it can be the primary or stand alone input. Suitable inputs 26 can include sensed data of blood pressure, pulse rate, EKG, peristaltic wave rate, respiration rate, various blood gases including blood oxygen saturation and $CO_2$ levels. In use, input 26 provides an additional signal that can be used to fine tune or otherwise adjust pacing signals 100s generated by the pacemaker. For example, sensed data on blood pressure or pulse rate can be used to adjust the rate of pacing signal 100s. In some cases, input 26 can actually be used as an override or primary signal such as when pulse rate or blood pressure have fallen below a particular threshold.

In various stimulating or pacing applications using window 21, an optical signal 28 can be sent from the window to provide stimulation to one or more tissue sites T such as the brain, optic nerve, eye, ganglia, spine or other like site. Signals 28 can be used to treat a variety of neurological disease and conditions including epilepsy, migraine headaches and chronic pain. In particular applications, optical signals 28 can be used to treat, inhibit or prevent epileptic or other neurological seizures by providing an optical input to a foci or surrounding tissue in the brain causing the seizure. Optical signals 28 can also be used in combination with one or more electrical signals 29 which are delivered to tissue site T to treat one or more neurological or other conditions (e.g., cardiovascular, GI, etc.). The electrical signals 29 can be generated by device 100 or a separate device. They can also be synchronized with optical signals 28. Optical signals 28 can also be configured for pacing and can be sent to provide pacing of one or more tissue sites including the heart, stomach, intestine and other sites.

In one or more embodiments including an optical window 21, the window can include a coating or layer 24 configured to minimize the attachment of cells and proteins to the window so as to maintain the optical transparency of window 21 for long term periods of implantation. Coating or layer 24 can comprise low surface tension polymers such as PTFE, silicones and polyurethane formulated to be optically transparent or translucent and/or one or more eluting compounds used to maintain the patency of cardiovascular stents. Such compounds can include one or more of anti-neoplastics such as PACLITAXEL, immunosuppessives such as SIROLIMUS and healing factors such as VGEF. Drug eluting embodiments of coating 24 can be configured to elute drug for selectable periods of five to ten years or longer so as to maintain the optical transparency of window 21. Coating 24 can also be applied to nontransparent embodiments of substrate 20 so as to improve the biocompatibility of the substrate, in these embodiments coating 24 does not necessarily have to be transparent.

Figure 8A:
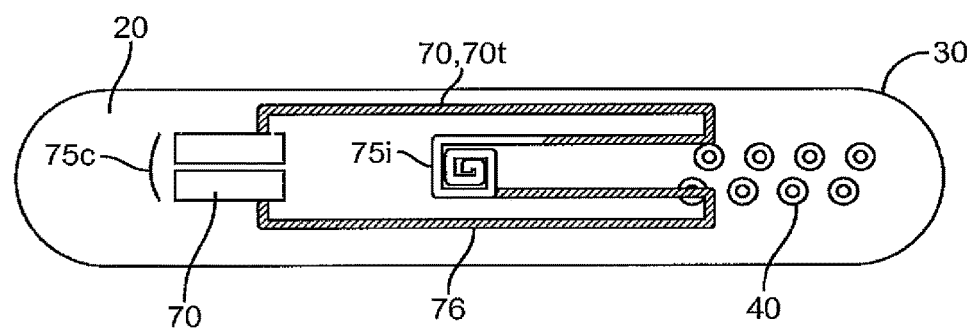
FIG. 8a is top view of the lid structure illustrating use of conductive portions to fabricate one or more electrical components including a capacitor and an inductor.
Figure 8B:
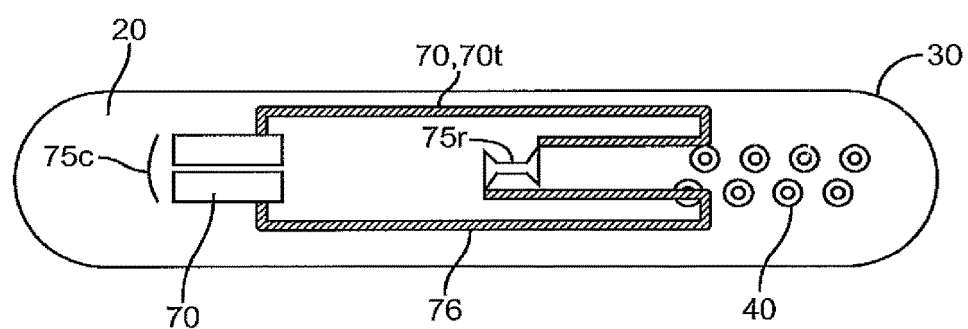
FIG. 8b is top view of the lid structure illustrating use of conductive portions to fabricate one or more electrical components including a capacitor and a resistor.
Figure 8C:
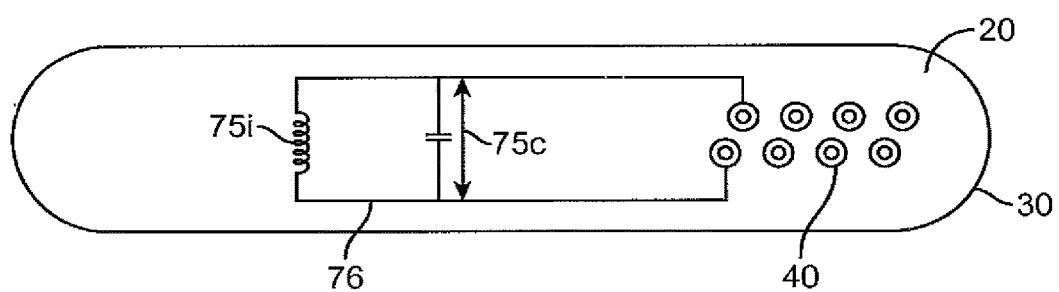
FIG. 8c is a schematic view of the lid structure illustrating use of conductive portions to fabricate an LC circuit.
Figure 9A:
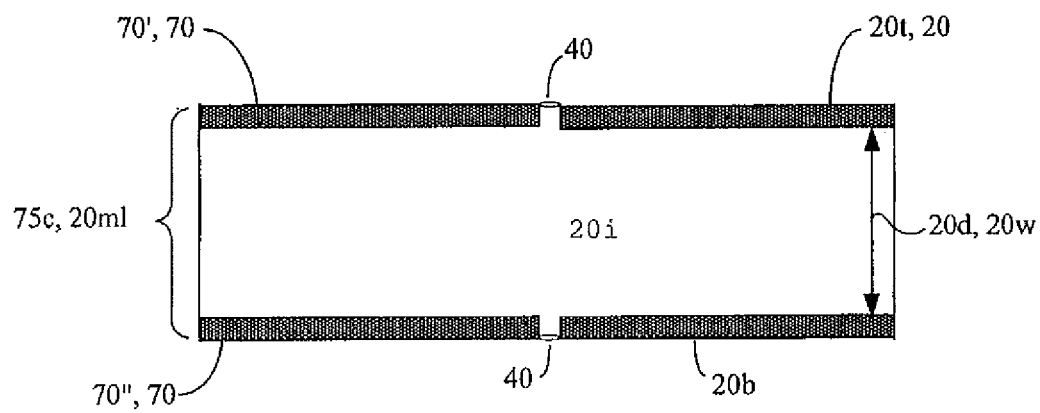
FIG. 9a is a cross sectional view illustrating an embodiment of a capacitor constructed by fabricating conductive portions on opposite surfaces of the substrate.
Figure 9B:
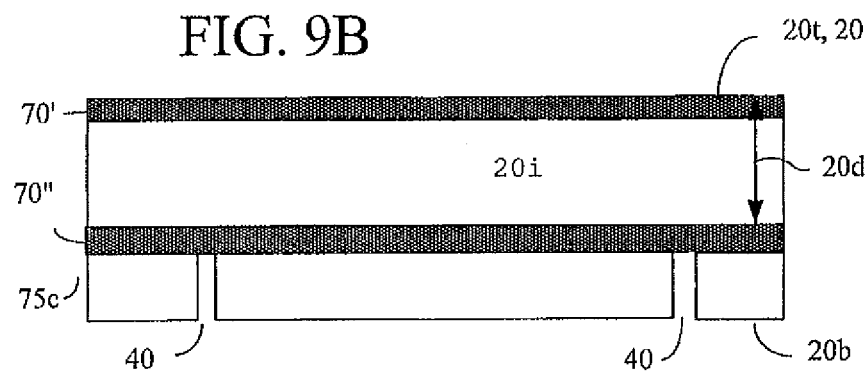
FIG. 9b is a cross sectional view illustrating an embodiment of a capacitor constructed by fabricating conductive portions within the interior of the substrate.
Figure 9C:
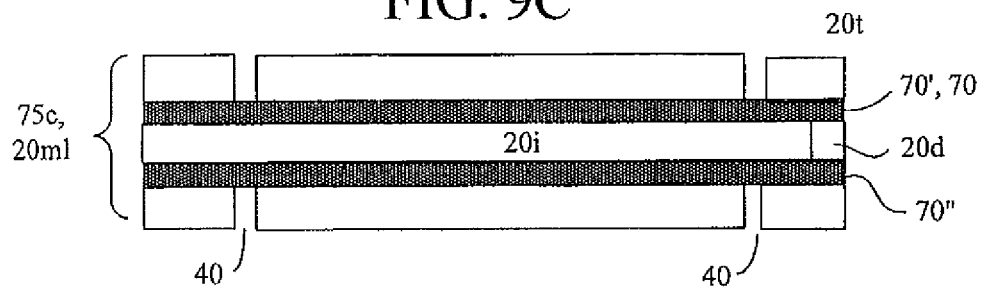
FIG. 9c is a cross sectional view illustrating an embodiment of a capacitor constructed by fabricating a first conductive portion on the surface of the substrate and a second conductive portion within the interior of the substrate.

As is described above, conductive portions 70 can be used to fabricate a number of electrical components 75 on or within substrate 20. Referring now to FIGS. 8-10, in various embodiments these components can include capacitors 75c, resistors 75r, inductors 75i and antennas 75a. Capacitors 75c can be fabricated by placement of a first and second conductive portion 70' and 70" at a selectable distance 20d along the thickness 20w of the substrate 20 to produce a selectable amount of capacitance. In various embodiments, capacitor 75c can be fabricated by positioning portions 70' and 70" on the top and bottom surfaces 20t and 20b of the substrate (FIG. 9a), within the interior 20i of the substrate (FIG. 9b), or by positioning one conductive portion can be placed on the surface and another within interior 20i (FIG. 9c).

Inductors 75i can be fabricated using a conductive trace 75t having a spiral pattern. Resistors 75r can be fabricated by narrowing the thickness of conductive trace or use of resistant materials in the trace. Multiple components 75 can be fabricated on the substrate to construct one or more circuits 76, such an LC, RC, or LRC circuit. In various embodiments, circuits 76 can be coupled to the connecting pins 50 to provide a filtering function (e.g., high pass, low pass, etc.) or other function for each pin or a selectable group of pins. In this way, the space requirements within housing 110 can be reduced in that circuits which would typically require multiple separate components can now be fabricated directly on the substrate 20.

Figure 10A:
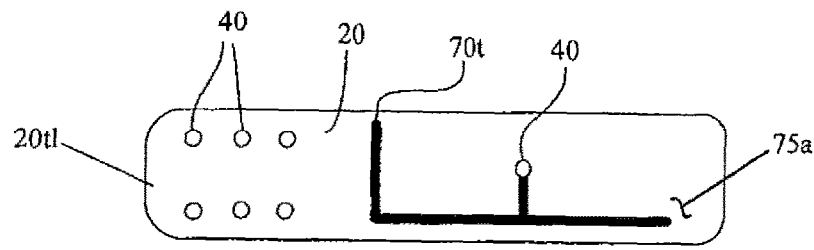
FIGS. 10a-10e illustrate various layers of an embodiment of a multilayer monolithic substrate having various components on each layer.
Figure 10B:
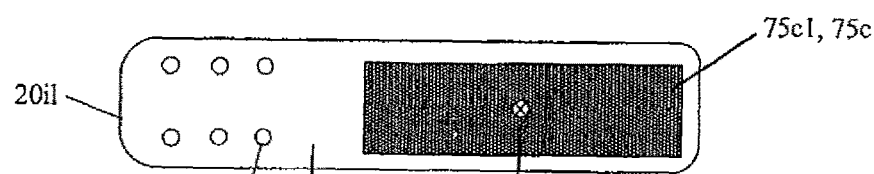
Figure 10C:
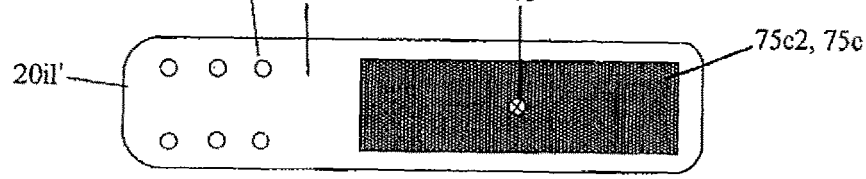
Figure 10D:
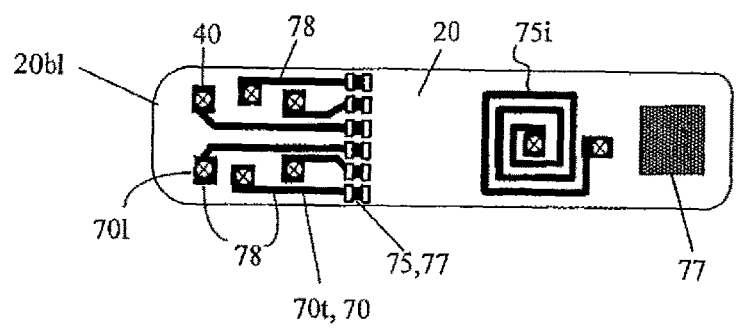
Figure 10E:
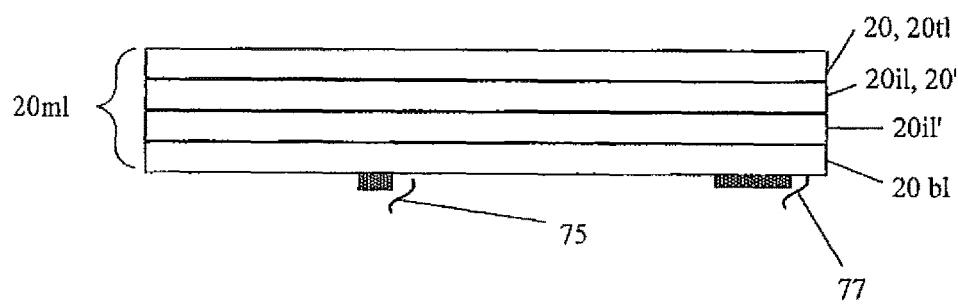

In various embodiments, substrate 20 can comprise a multilayer substrate 20ml with fabricated conductive portions 75 arranged to make or more components 75 on each layer 20. FIGS. 10a-10e show aspects of such embodiments. FIG. 10a illustrates a top layer 20tl, including an antenna 75a. FIG. 10b illustrates an interior layer 20il having a first capacitor plate 75c1. FIG. 10c illustrates another interior layer 20il' having a second capacitor plate 75c2 so as to comprise a capacitor 75c. FIG. 10d illustrates a bottom layer 20b1 including a connector architecture 78 for an attached component 75 or device 77. FIG. 10e shows the entire multilayer substrate 20ml along with attached components 75 and devices 77. Use of a multilayer substrate 20m provides for additional space savings since multiple components 75 which otherwise occupy space in housing 110 can now be positioned in the substrate 20 which comprises a wall 110w of housing 110.

The individual layers 20 of multilayer substrate 20ml can be mechanically connected by use of inserted pins 50 projecting through vias 40. Pins 50 can also be used to make the electrical connection between components 75 on each substrate layer 20. In use, embodiments of multilayer substrate 20ml allow for the additional savings of space within housing 110 since there are additional substrate layers 20 for fabrication of components 75 which would otherwise take up space in the housing. Also, multiple electrical components 75 and circuits 76 can be coupled via means of conductive portions 70 and/or pins 50 rather bulkier wires. Further space saving can be achieved by the fact that components 75 can be placed in very close proximity either on the same substrate layer 20 or different substrate layers 20' of a multilayer substrate 20ml. This too eliminates the need for wires and/or the need for other forms of bulky or lengthy electrical connection.

As describe above, in various embodiments, substrate 20 or multilayer substrate 20ml can be configured to provide a connector architecture 78 used to electrically connect various components 75 and devices 77 to substrate 20 or a multilayer substrate 20ml. Architecture 78 can be configured for electrical connection to specific electronic devices such as microprocessors, memory devices (e.g., ROM, RAM, DRAM, etc.), DSP's, AD converters and like devices. This can be achieved by configuring one or more connecting points 78p in the architecture 78 to align with corresponding connecting points on devices 77 so that device 77 aligns with architecture 78. Connecting points 78p may also align with one or more vias 40 to allow for connection to pins 50 and thus a connection to electrical components and leads outside housing 50. In use, architecture 78 allows for spacing savings in several respects. First, it can eliminate the need for an external connector (external in this case means external to the connected device, not necessarily external to the housing), such as a flexible connector, that some pace makers employ to make connections between electrical devices and components inside the pacemaker housing and components and leads outside the housing. Also architecture 78 allows components 75 and devices 77 to be placed in multiple spatial orientations (e.g., in multiple planes) so as to optimize the use of space within the housing 110. For example, architecture 78 may allow the use of a device 77 to be placed in vertical orientation which would not otherwise fit in a horizontal orientation due to the narrow thickness of some pacemaker housings. They may also allow connected components to be placed in different spatial orientations from other devices comprising the circuitry 130 of pacemaker 100p. Additionally, they can allow the use of previously unusable space by being able to connect components directly to the walls 110w of housing 110.

Figure 11A:
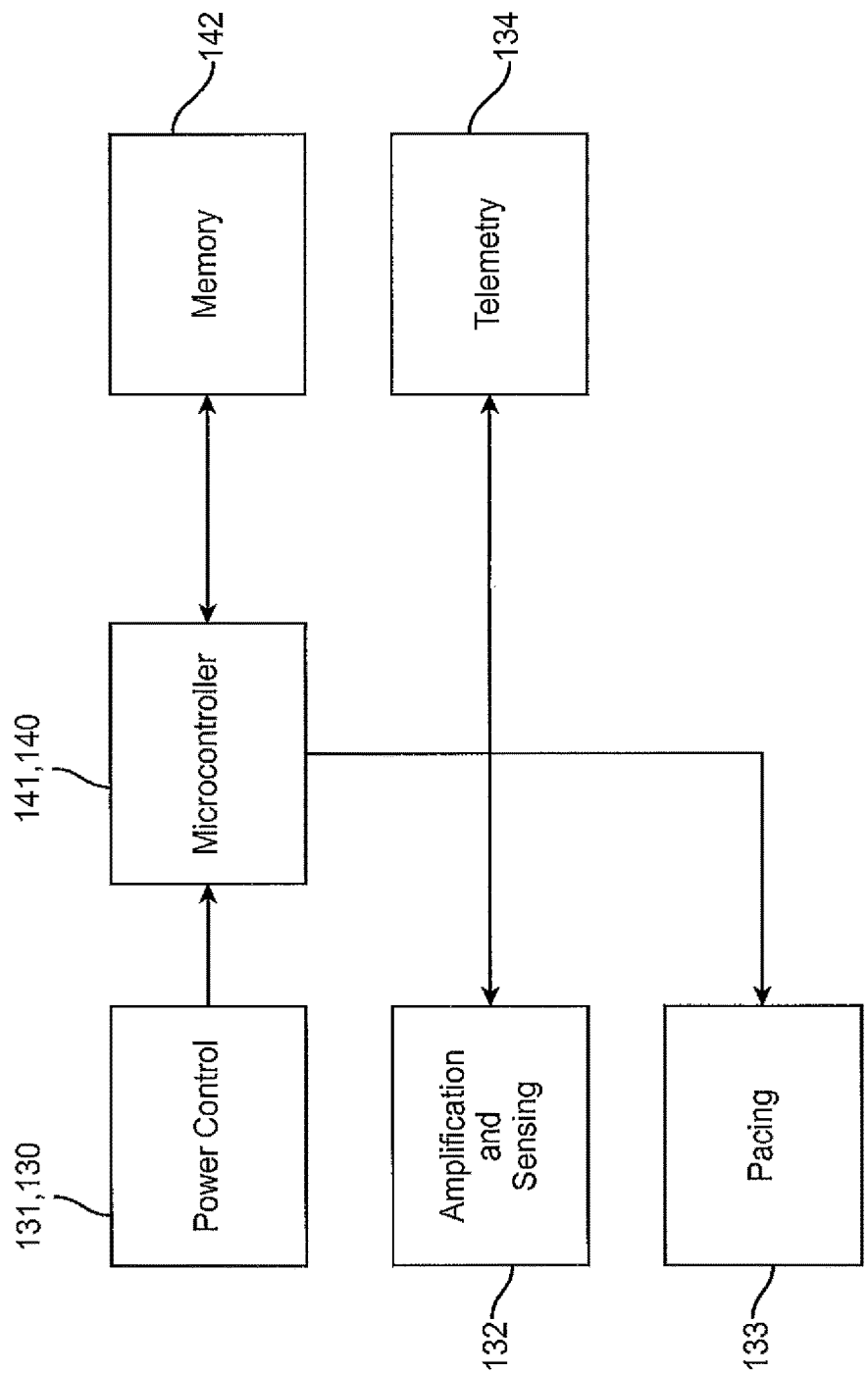
FIG. 11a is a block diagram illustrating some of the typical circuitry on a pacemaker or other implantable pacing or stimulating device.
Figure 11B:
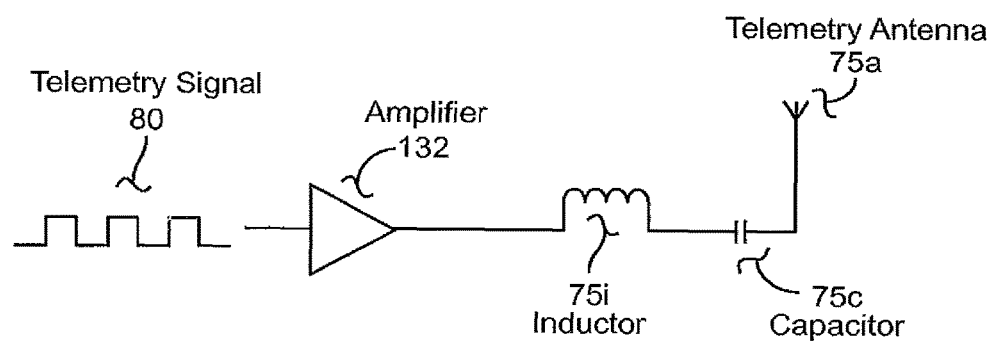
FIG. 11b is a schematic view of the lid structure illustrating integration of circuitry fabricated on the substrate with circuitry of the medical implant.

Referring now to FIG. 11a, some of the typical circuitry 130 and electronic devices 140 in a pacemaker 100p or like device can include power control circuitry 131, amplification and sensing circuitry 132, pacing circuitry 133, telemetry circuitry 134, micro-controller/micro-processor devices 141 and memory devices 142. In various embodiments, one or more of the components 75 and circuits 76 fabricated on the substrate 20 can form an integral part of these or circuitry of components of pacemaker 100. Referring now to FIG. 11b, in one embodiment, one or more of an antenna 75a, inductor 75i, capacitor, 75c that are fabricated on substrate 20 can be an integral part of into a telemetry circuit 134 of pacemaker 100p or other medical implant. In use, such integral configurations can achieve space and cost savings because the need for multiple separate electrical components and associated connections is reduced.

Figure 12:
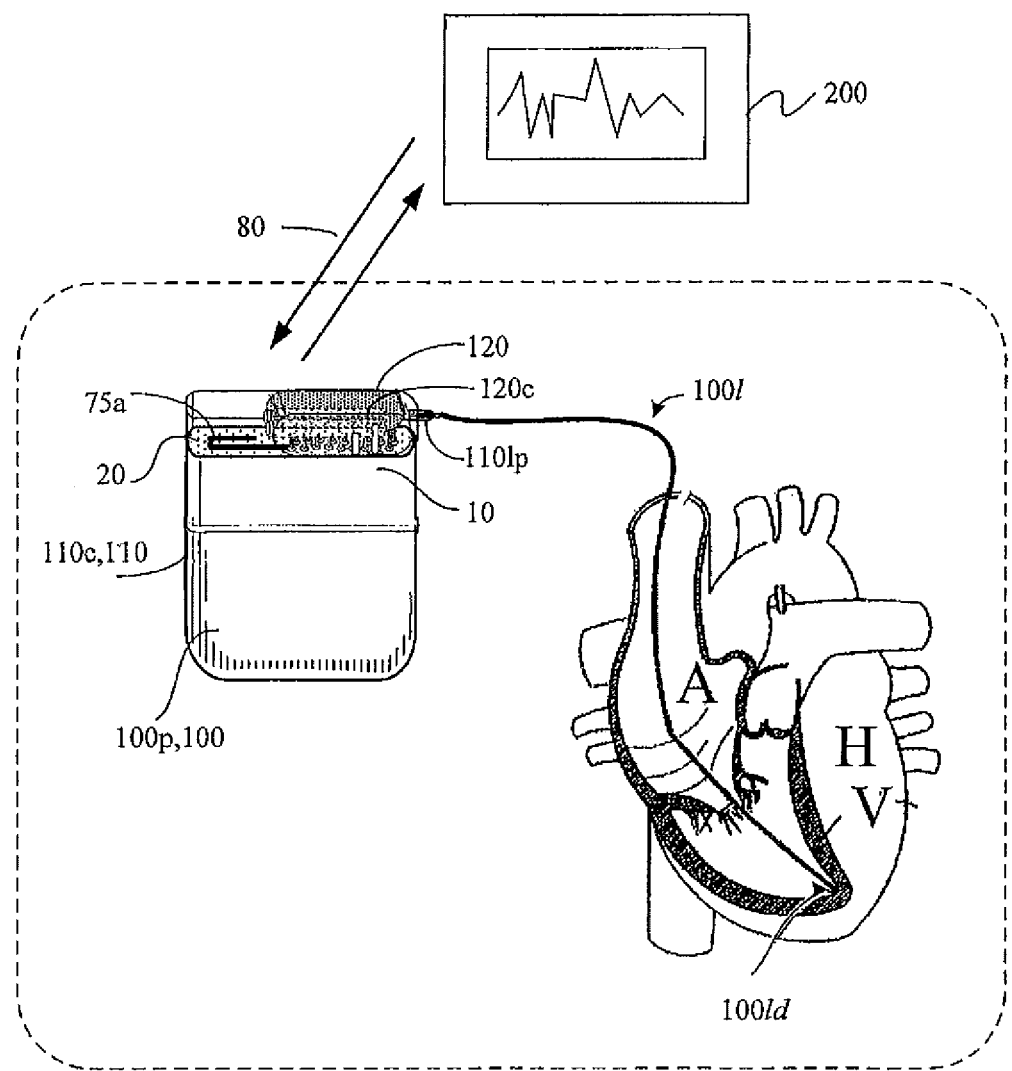
FIG. 12 is a perspective view illustrating use of the antenna to communicate between a medical implant and an external communication device.

Referring now to FIGS. 1, 10a and 12, in many embodiments, substrate 20 can include an antenna 75a desirably fabricated on substrate top side 20t so as to send and receive signals 80 to and from an external communication device 200 when the pacemaker is implanted in the body. Antenna 75a will typically comprise at least one conductive trace 70t that is sized and otherwise configured to send and receive signals in a selectable frequency range such as the 400 MHz to 6 GHz frequency range with a specific embodiment of 402 to 405 MHz corresponding to the MICS standard established by the FCC. Other frequency ranges are also contemplated corresponding to one or more standards for medical electronics or related products such as those corresponding to the Medical Data Service (MDS), Wireless Medical Telemetry (WMT) and Industrial, Scientific & Medical (ISM) standards. This can be achieved by fabricating the antenna to have one or more turns and selection of the permittivity of the substrate material as is discussed herein. The trace 70t for antenna 75a can have a have a variety of shapes including linear, rectangular, U-shaped, circular or like shape and can include one or more turns so as to form a series of inward concentric shapes. The length and width of structure 10 can be sized to allow for the selected size and shape of selected antenna 70 while still allowing distance between the antenna and the perimeter 10P of structure 10.

The shape and other properties of antenna 70a (e.g., impedance, etc) are configured to be able to send and receive signals 80 between the implant and a external communication device 200 positioned several or more feet away. In many embodiments, this can be achieved by configuring the antenna to send and receive signals in the MICS frequency range (about 402 to 405) which allows for communication at distances of about 2 meters or so. In various embodiments communication device 200 can comprise a PDA, computer or other RF based communication device. The signals 80 which are sent and received can be used to send data from pacemaker or other device 100, perform various diagnostic test on the pacemaker and reprogram the pacemaker.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the lid structure have broad application to a number of implanted medical products including implantable pulse generators, pace makers, cardioverter-defibrillators and other cardiac devices, gastric pacemakers and other gastric stimulators, spinal pain relief and other spinal stimulators, implanted neural stimulators for Parkinson's disease and other neural and muscle stimulators and cochlear implants Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for stimulation of neural tissue to treat a neurological condition, the method comprising:
providing a stimulator apparatus configured to operate in or on the neural tissue, the stimulator apparatus including a substrate comprising a transparent dielectric material and including an optical window with an exterior configured to maintain an optical transparency of the optical window for an extended period of time, the stimulator apparatus configured to generate one or more optical stimulation signals; and
delivering an optical stimulation signal generated by the stimulator apparatus to the neural tissue through the optical window to treat the neurological condition and measure optical properties of the neural tissue.

2. The method of claim 1, wherein the optical window further includes a coating configured to minimize attachment of cells to the optical window, the method further comprising:
eluting a compound from the coating for an extended period of time so as to maintain optical transparency of the optical window.

3. The method of claim 2, further comprising herein the compound is eluted from the coating for a period up to ten years so to maintain the optical transparency of the optical window.

4. The method of claim 1, wherein the optical stimulation signal is delivered to brain tissue to treat the neurological condition.

5. The method of claim 1, wherein at least a portion of the stimulator apparatus is implanted in a skull.

6. The method of claim 1, wherein at least a portion of the stimulator apparatus is implanted in a brain.

7. The method of claim 6, wherein the optical stimulation signal is further delivered to allow for measurement of changes in optical properties of brain tissue.

8. The method of claim 1, wherein the optical stimulation signal is configured to treat an epileptic seizure.

9. The method of claim 8, wherein the optical stimulation signal is configured to inhibit or prevent the epileptic seizure.

10. The method of claim 8, wherein the optical stimulation signal is delivered to a foci in a brain causing the epileptic seizure.

11. The method of claim 10, wherein the optical stimulation signal is delivered to tissue surrounding the foci in the brain causing the epileptic seizure.

12. The method of claim 1, further comprising:
delivering an electrical stimulation signal to brain tissue to treat the neurological condition.

13. The method of claim 12, wherein the electrical stimulation signal is generated by the stimulator apparatus.

14. The method of claim 12, wherein the electrical stimulation signal is synchronized with the optical stimulation signal.

15. The method of claim 12, wherein the electrical stimulation signal and the optical stimulation signal produce an aggregate effect in the neural tissue to treat the neurological condition.

16. The method of claim 1, wherein the optical stimulation signal is configured to treat a migraine headache.

17. The method of claim 1, wherein the optical stimulation signal is configured to treat chronic neurological pain.

18. The method of claim 1, wherein the optical window is coupled to an optical conduit, the method further comprising:
    delivering the optical stimulation signal to the neural tissue through the optical conduit.

19. The method of claim 18, wherein at least a portion of the optical conduit is implanted in the neural tissue.

20. The method of claim 18, wherein the optical conduit comprises an optical fiber.

21. The method of claim 7, further comprising:
    measuring the optical properties of the brain tissue through the optical window, the optical properties including one or more of a blood glucose level or a blood oxygen saturation.

22. The method of claim 21, further comprising:
    modulating the optical stimulation signal in response to the measured optical properties of the brain tissue exceeding or dropping below a predetermined threshold.

23. The method of claim 1, wherein the substrate is positioned near a wall of a housing.

24. The method of claim 23, wherein the substrate abuts a wall of a housing.

* * * * *